United States Patent
Jackson et al.

(10) Patent No.: US 11,116,547 B2
(45) Date of Patent: *Sep. 14, 2021

(54) PIVOTAL BONE ANCHOR ASSEMBLY WITH BOTTOM LOADED INSERT AND PIVOTLESS RETAINER

(71) Applicant: Roger P. Jackson, Prairie Village, KS (US)

(72) Inventors: Roger P. Jackson, Prairie Village, KS (US); James L. Surber, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/685,695

(22) Filed: Nov. 15, 2019

(65) Prior Publication Data

US 2020/0078052 A1    Mar. 12, 2020

Related U.S. Application Data

(63) Continuation of application No. 16/118,079, filed on Aug. 30, 2018, now Pat. No. 10,478,229, which is a continuation of application No. 14/730,981, filed on Jun. 4, 2015, now Pat. No. 10,064,658.

(60) Provisional application No. 62/007,623, filed on Jun. 4, 2014.

(51) Int. Cl.
*A61B 17/70* (2006.01)
*A61B 17/86* (2006.01)

(52) U.S. Cl.
CPC ...... *A61B 17/7037* (2013.01); *A61B 17/7032* (2013.01); *A61B 17/864* (2013.01)

(58) Field of Classification Search
CPC ............ A61B 17/7034; A61B 17/7035; A61B 17/8685; A61B 17/864; A61B 17/7037; A61B 17/7032
See application file for complete search history.

(56) References Cited

U.S. PATENT DOCUMENTS

| | | |
|---|---|---|
| 5,425,768 A | 6/1995 | Carpenter et al. |
| 6,429,257 B1 | 8/2002 | Buxton et al. |
| 8,075,599 B2 | 12/2011 | Johnson et al. |
| 8,444,681 B2 | 5/2013 | Jackson et al. |
| 8,556,938 B2 | 10/2013 | Jackson et al. |
| 8,636,778 B2 | 1/2014 | Gephart et al. |
| 9,597,119 B2 | 3/2017 | Jackson et al. |
| 9,949,760 B2 | 4/2018 | Jackson et al. |
| 10,039,572 B2 | 8/2018 | Harris et al. |

(Continued)

OTHER PUBLICATIONS

International Search Report and Written Opinion regarding PCT/US2015/056706, dated Jan. 6, 2016.

(Continued)

*Primary Examiner* — Julianna N Harvey
(74) *Attorney, Agent, or Firm* — Polsinelli PC

(57) ABSTRACT

A polyaxial bone anchor with a receiver, a shank, a pressure insert, a retainer for holding the shank in the receiver, and a closure. The receiver having at least one vertically aligned guide on a surface of an interior shank and insert receiving chamber. The insert having at least one shoulder that aligns with the guide and both properly positions the insert relative to the receiver during assembly and prevents the insert from axially rotating relative to the receiver.

20 Claims, 10 Drawing Sheets

(56) References Cited

U.S. PATENT DOCUMENTS

| | | | |
|---|---|---|---|
| 10,064,658 B2* | 9/2018 | Jackson | A61B 17/7037 |
| 10,478,229 B2* | 11/2019 | Jackson | A61B 17/7037 |
| 2002/0068975 A1 | 6/2002 | Teitelbaum et al. | |
| 2005/0277928 A1* | 12/2005 | Boschert | A61B 17/7037 |
| | | | 606/328 |
| 2007/0233085 A1 | 10/2007 | Biedermann et al. | |
| 2007/0270813 A1 | 11/2007 | Garamszegi | |
| 2007/0288012 A1 | 12/2007 | Colleran et al. | |
| 2008/0249576 A1* | 10/2008 | Hawkes | A61B 17/7037 |
| | | | 606/305 |
| 2009/0005817 A1 | 1/2009 | Friedrich et al. | |
| 2010/0087865 A1 | 4/2010 | Biedermann et al. | |
| 2010/0160980 A1 | 6/2010 | Walsh | |
| 2010/0222820 A1 | 9/2010 | Trieu | |
| 2011/0160778 A1 | 6/2011 | Elsbury | |
| 2011/0178559 A1 | 7/2011 | Barry | |
| 2011/0270321 A1* | 11/2011 | Prevost | A61B 17/7031 |
| | | | 606/305 |
| 2012/0109208 A1* | 5/2012 | Justis | A61B 17/7089 |
| | | | 606/264 |
| 2012/0143255 A1 | 6/2012 | Jackson et al. | |
| 2013/0110176 A1 | 5/2013 | Rezach et al. | |
| 2014/0128927 A1 | 5/2014 | Jackson | |

OTHER PUBLICATIONS

International Preliminary Report on Patentability regarding PCT/US2015/056706, dated Nov. 17, 2016.

* cited by examiner

PIVOTAL BONE ANCHOR ASSEMBLY WITH BOTTOM LOADED INSERT AND PIVOTLESS RETAINER

CROSS REFERENCE TO RELATED APPLICATIONS

This application is a continuation of U.S. application Ser. No. 16/118,079 filed Aug. 30, 2018, which is a continuation of U.S. application Ser. No. 14/730,981, filed Jun. 4, 2015, now U.S. Pat. No. 10,064,658, which claims the benefit of U.S. Provisional Application No. 62/007,623, filed Jun. 4, 2014, each of which is incorporated by reference in its entirety herein.

BACKGROUND OF THE INVENTION

Polyaxial bone screws and related anchors of various types have been used for supporting rods and other elongate members in spinal surgery. Some of these bone screws utilize a lower pressure insert to transfer locking forces from a rod or other structure above the insert to a shank below the insert, so as to lock the shank in a fixed angular configuration with respect to a receiver. A problem encountered with the insert is that during assembly of the insert into the receiver and/or during transport and/or during implantation of the anchor into a patient, the insert may undesirably rotate from a preferred alignment and configuration relative to the receiver.

SUMMARY OF THE INVENTION

A bone anchor assembly, especially a bone screw, includes a shank for implanting into a bone, a receiver for holding the shank and receiving an elongate connecting member such as a rod, a pressure insert with opposed upwardly extending arms and a closure. Preferably, the shank has a spherical head and polyaxially joins with the receiver and is held in the receiver by a retainer that may be joined to the receiver or the shank head. The receiver has upper arms that are spaced and form a channel for receiving the elongate member. The receiver arms include break-off extensions, although in some embodiments no extensions will be included. The closure is advancingly received between the arms and applies locking pressure to the elongate member which in turn applies the pressure to the insert that locks the position of the shank relative to the receiver. The closure can also be configured to apply locking pressure to the insert before independently applying locking pressure to the elongate member.

The insert is preferably uploaded into the receiver, but may be downloaded through the channel in certain embodiments. The insert has a plurality of and particularly four opposed generally vertically aligned corners or shoulders. The receiver has a plurality of and particularly four alignment and positioning guides that form regions for receiving the insert shoulders and that snugly slidingly mate with the shoulders on the insert as the insert is being axially or vertically loaded into the receiver. The insert shoulders and the receiver guides cooperate to properly position the insert in the receiver while preventing the insert from rotating axially relative to the receiver. The insert has upwardly extending arms form an insert channel that then aligns with a similar channel of the receiver to accept the elongate member.

Preferably, the shank is cannulated and is polyaxially moveably in the receiver during positioning and thereafter locked in place.

Figure 1:
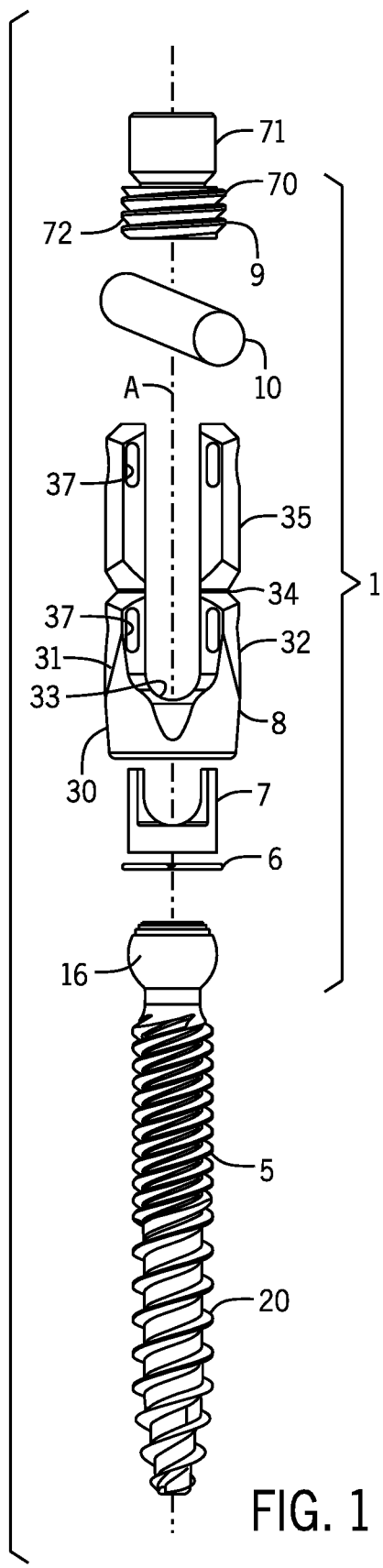
FIG. 1 is an exploded view of a bone screw including a shank, a receiver, a retainer, a pressure insert and a closure, shown in conjunction with a rod.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a bone anchor in accordance with the invention. While the illustrated anchor 1 is generally a polyaxial bone screw, it is foreseen that the invention could be utilized with other types of spinal implants that utilize pressure inserts, such as polyaxial bone hooks.

The bone anchor 1 comprises a shank 5, a retainer 6, a pressure insert 7, a receiver 8 and a closure 9 and is used with an elongate member 10.

Figure 3:
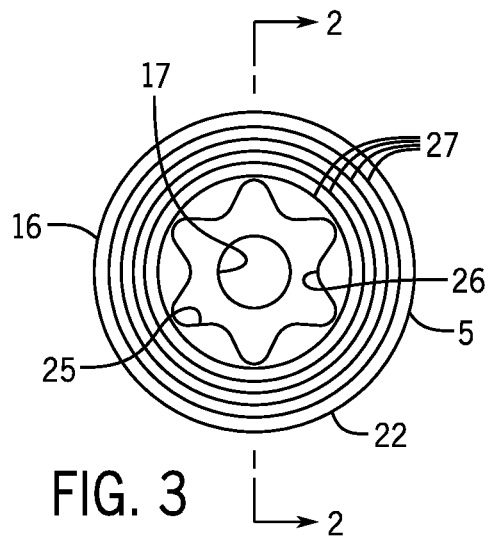
FIG. 3 is a top plan view of the bone screw.
Figure 2:
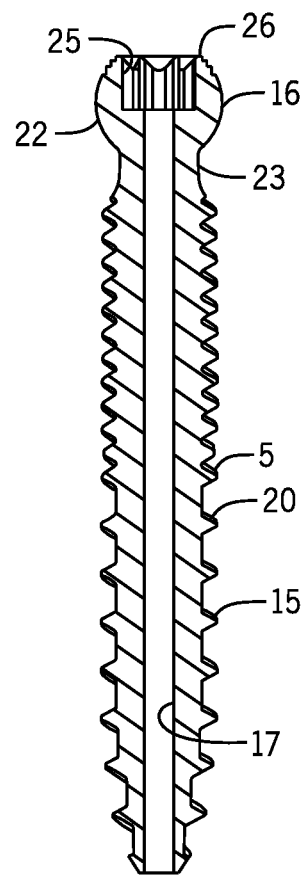
FIG. 2 is a cross sectional view of the bone screw taken along line 2-2 of FIG. 3.
Figure 4:
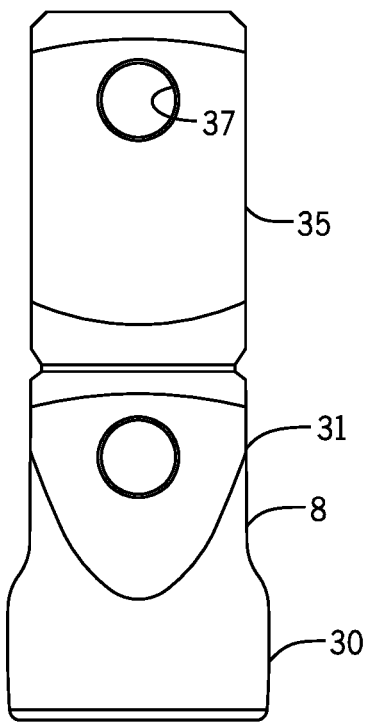
FIG. 4 is a side elevational view of the receiver.
Figure 5:
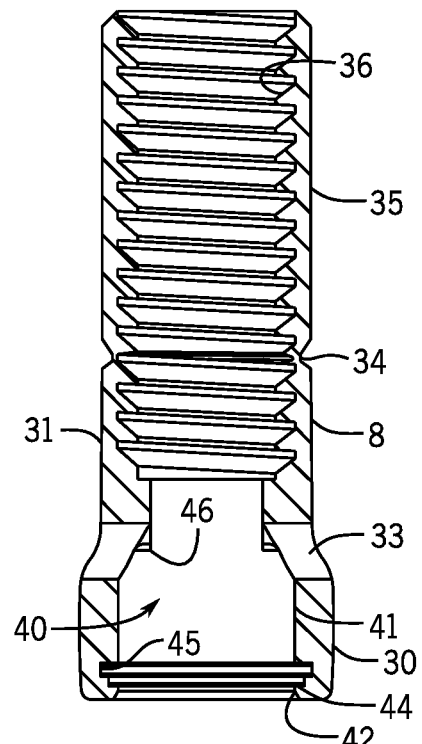
FIG. 5 is a cross sectional view of the receiver, taken along line 5-5 of FIG. 6.
Figure 6:
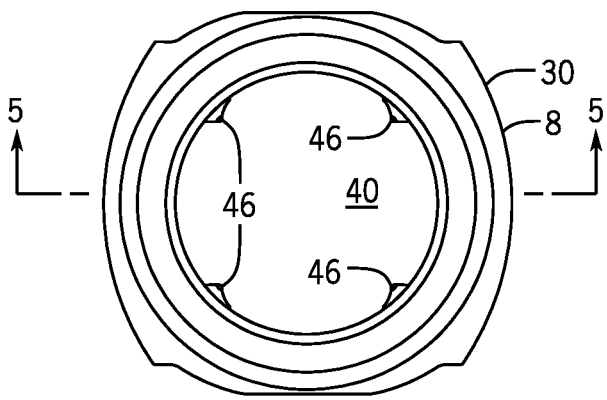
FIG. 6 is a bottom plan view of the receiver.
Figure 7:
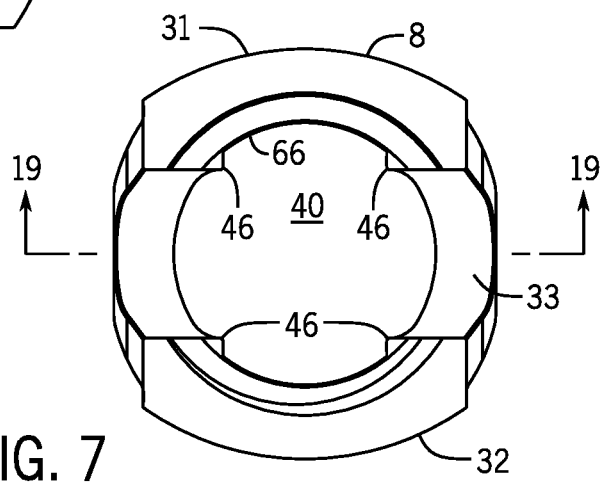
FIG. 7 is a top plan view of the receiver.
Figure 8:
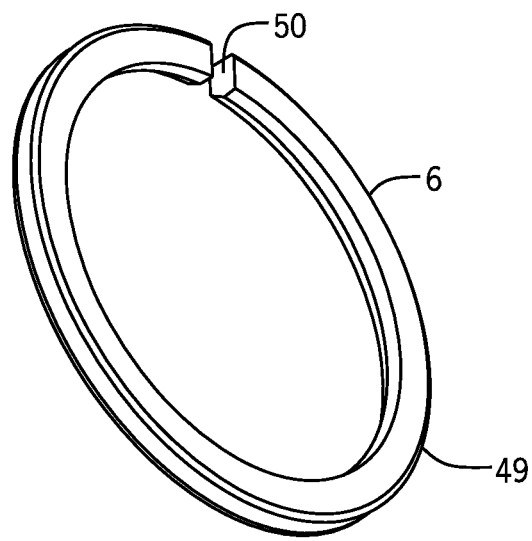
FIG. 8 is a perspective view of the retainer.
Figure 9:
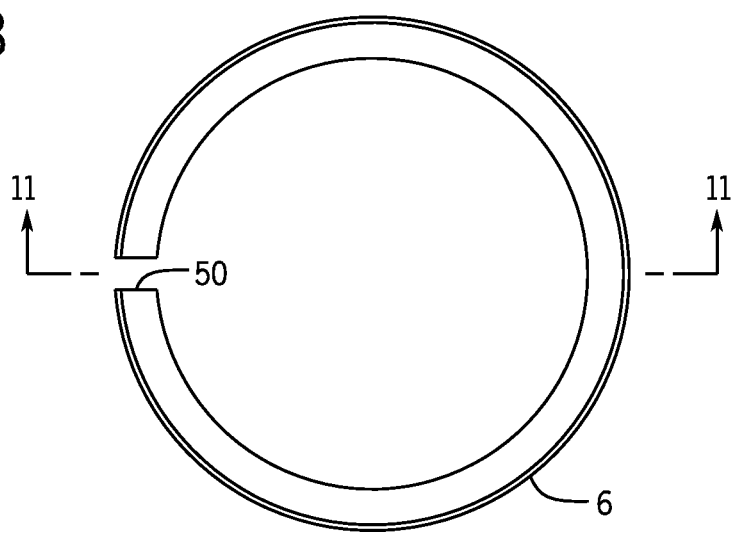
FIG. 9 is a top plan view of the retainer.
Figure 10:
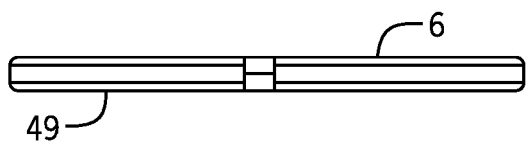
FIG. 10 is a side elevational view of the retainer.
Figure 11:
FIG. 11 is a cross sectional view of the retainer, taken along line 11-11 of FIG. 9.
Figure 12:
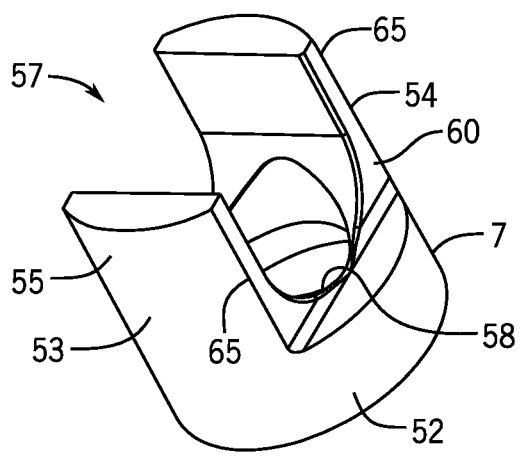
FIG. 12 is a perspective view of the insert.
Figure 13:
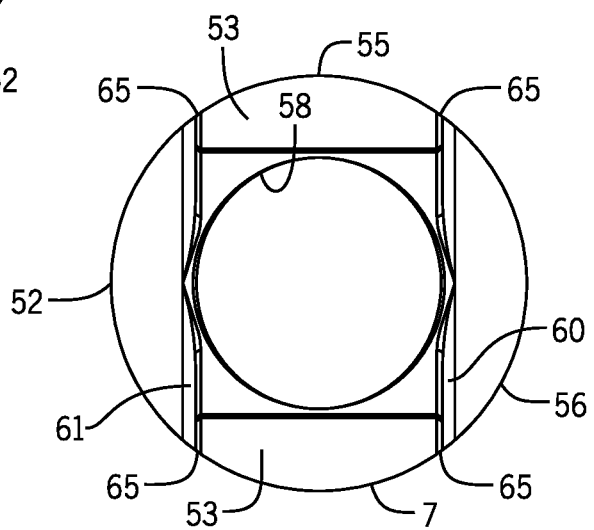
FIG. 13 is a top plan view of the insert.
Figure 14:
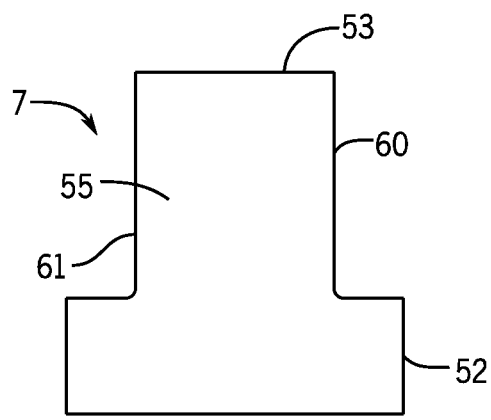
FIG. 14 is a side elevational view of the insert.
Figure 15:
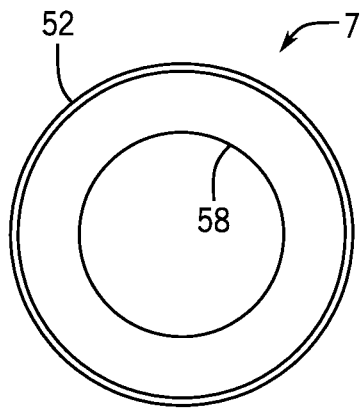
FIG. 15 is a bottom plan view of the insert.
Figure 16:
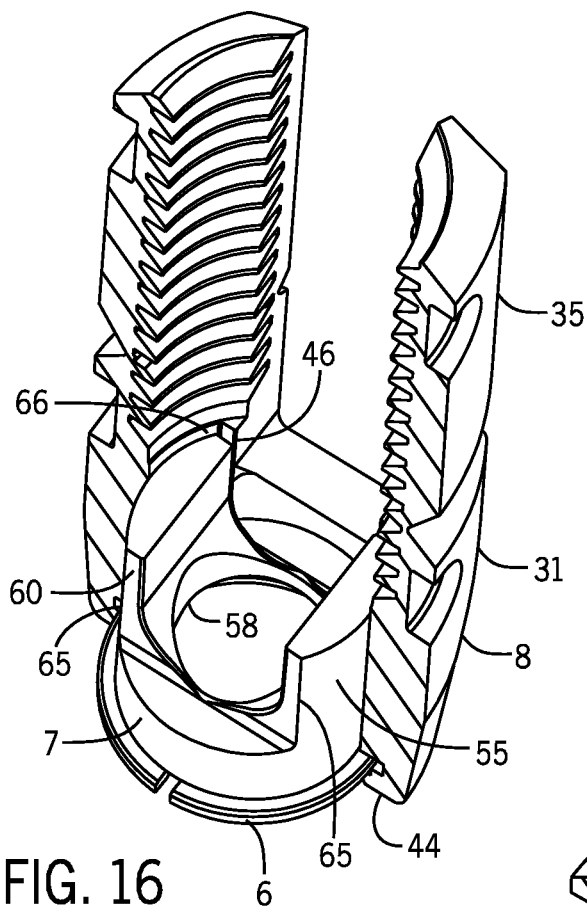
FIG. 16 is a perspective view of the receiver, insert and retainer with portions of the retainer cut away to show cooperation of the parts at a stage whereat the insert is being positioned in the receiver.
Figure 17:
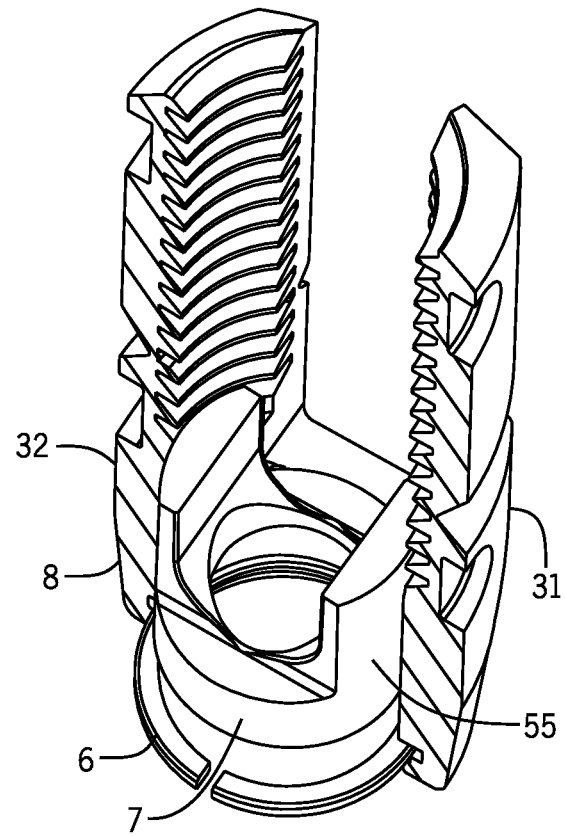
FIG. 17 is a perspective view of the receiver, insert and retainer with portions of the retainer cut away to show cooperation of the parts at a stage whereat the insert is in an upper most position relative to the receiver.
Figure 18:
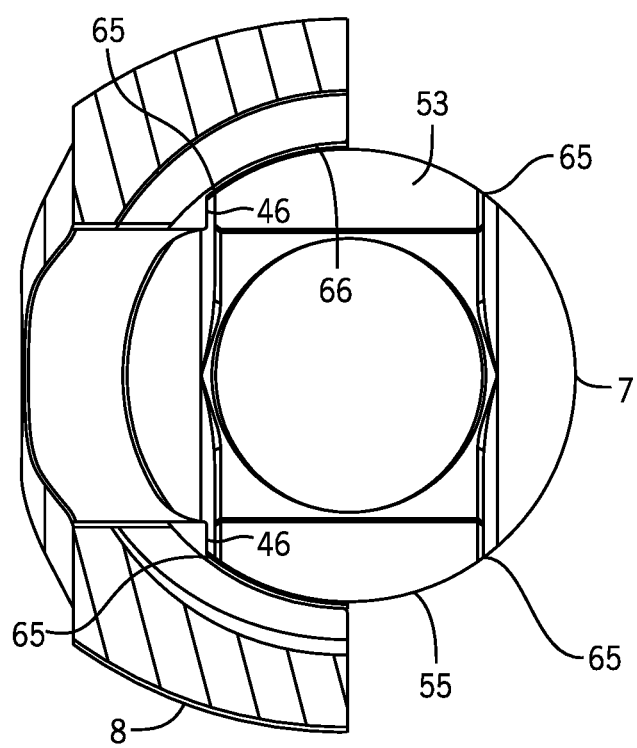
FIG. 18 is a partial top plan view of the combined receiver and insert with portions of the retainer broken away to illustrate mating of the insert and retainer.

The shank 5 as seen in FIGS. 1 to 3 has a lower portion 15 and an upper portion 16 with an axial bore 17 throughout so as to cannulate the shank 5. The lower portion 15 has a flighting or helical wound thread 20 which is doubled in the upper half for threading into a vertebra of a patient.

The shank upper portion 16 includes a bulbous and partially spherical head 22 that radially extends outward from a neck 23 joining the head 22 to the lower portion 15. Axially centered and extending downward from the top of the head 22 is a tool receiving structure 24 with radially inward extending alternating lobes 25 for receiving and gripping a tool (not shown) used to drive the shank 5 into a bone of a patient. An upper surface 26 of the head 22 has a series of concentric gripping ribs 27 for enhancing frictional contact with the insert 7 which can be made of a somewhat softer metal compared to that of the head.

Illustrated in FIGS. 4 to 7 is the receiver 8. The receiver 8 has a lower body 30 and a pair of upstanding spaced arms 31 and 32 forming an elongate member receiving channel 33. In the illustrated embodiment the channel 33 is generally U-shaped, but the shape can be varied to accommodate elongate members of different shapes. Attached by break off junctures 34 to the arms are extensions 35. On facing inner surfaces of the arms are guide and advancement structure which in the illustrated embodiment are helical wound reverse angle thread forms 36, but can be various types of threads, such as a conventional V thread, buttress or square threads or helical flanges. Tool grasping apertures 37 are located on the sides of each arm 31 and 32.

Located in the receiver body 30 is a chamber 40 formed by side walls 41 that opens both into the channel 33 above and to the exterior through a lower opening 42. During assembly of the anchor 1, the chamber 40 receives both the shank head 22 and the insert 7. The lower end of the chamber has a first groove 44 and a larger second groove 45 that are axially aligned with a central Axis A of the receiver, the purpose of which will be discussed later. It is foreseen that the shank can be downloaded into the receiver and not require a retainer, and that the receiver does not have but one groove for the retainer.

Located on the chamber side walls 41 near an upper side thereof are four spaced and radially inward projecting projections or guides 46. The guides 46 cooperate with the insert 7 as discussed below.

The retainer 6 is shown in FIGS. 8 to 11. The retainer 6 is an open resilient ring 49 with a gap or break 50 to allow contraction and expansion thereof. The ring 49 is compressed and loaded into the receiver. This can occur before or after loading the shank in some embodiments. In the embodiment shown, the ring is loaded first and passes over the shank head 22 during loading of the head 22 into the chamber 40 thereby capturing the shank. During expansion, the ring 49 is received in the larger receiver groove 45 after which the ring 49 is lowered into the smaller groove 44 which is about the same diameter as the ring 49 so that the ring 49 fits snugly therein to prevent repeated expansion. In this manner, the ring 49 holds the shank head 22 in the receiver 8 and allows the shank 5 to pivot relative to the receiver 8 during positioning and before locking.

The insert 7 is best seen in FIGS. 12 to 18. The insert 7 includes a lower body 52 with a pair of spaced upstanding arms 53 and 54. The arms 53 and 54 and body 52 have a continuous radially outer surface 55 on each side which are substantially smooth and vertically or axially aligned, but radially spaced from the Axis A. The arms 53 and 54 form a central U-shaped channel 57 therebetween and there is a central axially aligned and centered bore 58.

On either side of the arms 53 and 54 are flat surfaces 60 and 61. At the intersection of the surfaces 60 and 61 with the surfaces 55 and 56 are formed four corners or shoulders 65. The shoulders 65 extend along a length of the insert 7 and are vertically or axially aligned. Each of the shoulders 65 are sized and shaped to vertically slide, but snugly mate with the receiver guides 46. This allows the insert 7 to move vertically during loading into the receiver 8 and during certain positioning required during assembly and implantation of the anchor 1, but prevents the insert 7 from rotating about the axis A relative to the receiver 8. This relationship is perhaps best seen in FIG. 16 wherein the left rear shoulder 65 is seen sliding vertically along the receiver surface 66 and guide 46, but is constrained from axial rotation by the abutment of the shoulder 65 with the guide 46.

The closure 9 is best seen in FIG. 1. The closure 9 has a body 70 with a head 71 that has a tool engagement surface 72 and that breaks from the body 70 at a predetermined torque. Helically wound about the body 70 is a guide and advancement structure 73 which operably mates with the guide and advancement structure 36 on the receiver arms 31 and 32.

The elongate member 10 is for extending between various implants (not shown) in an overall system. The illustrated elongate member 10 is a circular rod, although members of various construction and shape may be utilized.

FIGS. 19 to 27 show various stages in the assembly and utilization of the anchor 1 in a snap-on screw embodiment.

Figure 19:
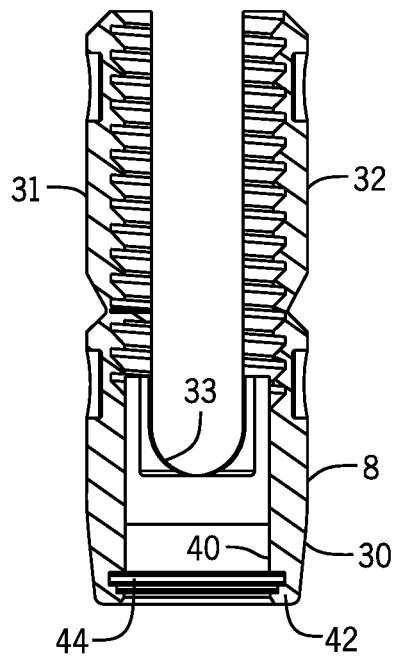
FIG. 19 is a cross section of a side elevational view of the receiver, taken along line 19-19 of FIG. 7 showing the receiver before assembly of the bone anchor.
Figure 20:
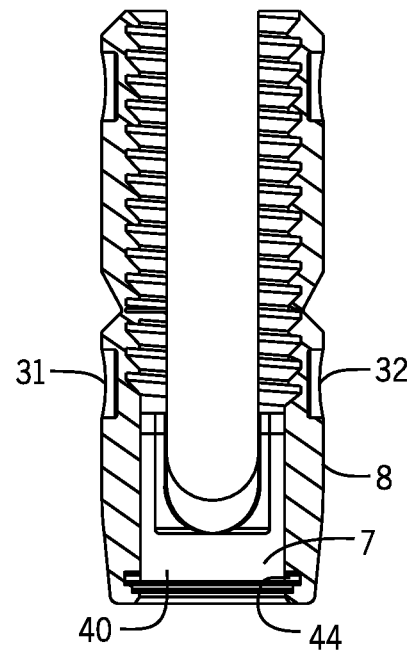
FIG. 20 is a cross section of the receiver, as in FIG. 19, showing a first stage of the positioning of the insert in the receiver.
Figure 21:
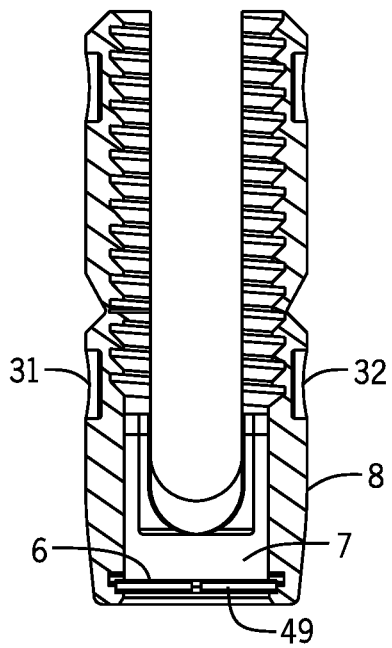
FIG. 21 is a cross section of the receiver as in FIG. 20 showing a second stage of the positioning of the retainer in the receiver.
Figure 22:
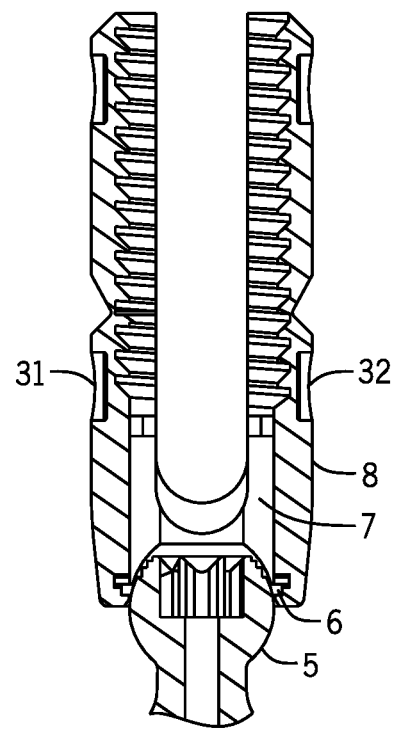
FIG. 22 is a cross section of the receiver as in FIG. 20 showing a third stage of the positioning of the shank head in the receiver with the shank first entering the receiver.

The receiver 8 is shown by itself in FIG. 19. In FIG. 20 the pressure insert 7 is uploaded through the opening 42 into the chamber 40. In FIG. 21, the retainer ring 49 is placed in the chamber 40. In FIG. 22, the top of the shank 5 is partially inserted into the chamber 40 and abuts against the retainer 6.

Figure 23:
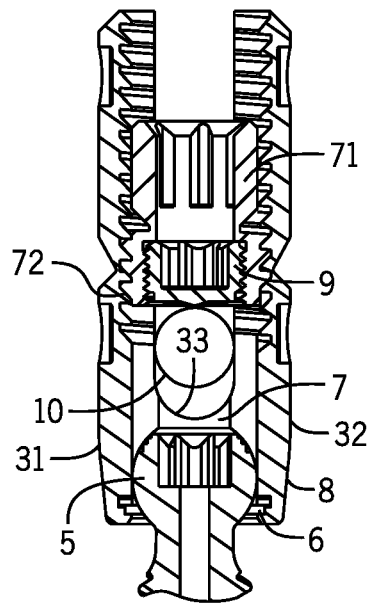
FIG. 23 is a cross section of the receiver as in FIG. 19 showing a fourth stage of the positioning of the insert in the receiver with the shank head having passed through the retainer and being captured in the receiver.
Figure 24:
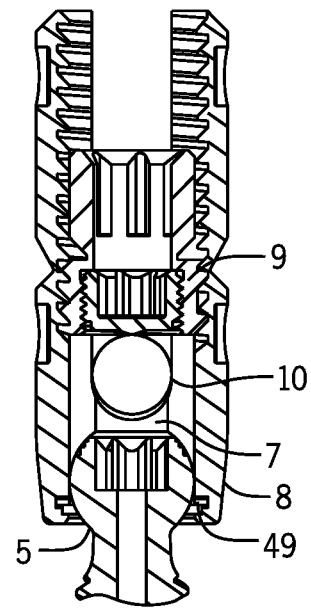
FIG. 24 is a cross section of the receiver as in FIG. 19 showing view of a fifth stage of the positioning of the insert in the receiver with a rod and closure added and the closure applying pressure only to insert.

In FIG. 23, the ring 6 has captured the shank head after moving up into the larger receiver groove 45 and coming back down into the smaller groove, while the insert moved upward being aligned and guided by the guides 46. In FIG. 24, the shank head is, again, shown fully captured and the ring 49, which is located around the lower half of the head 22, is shown fully seated in the lower and smaller groove 44. The closure is seen compressing the insert to lock the shank with respect to the receiver before locking the rod.

Figure 25:
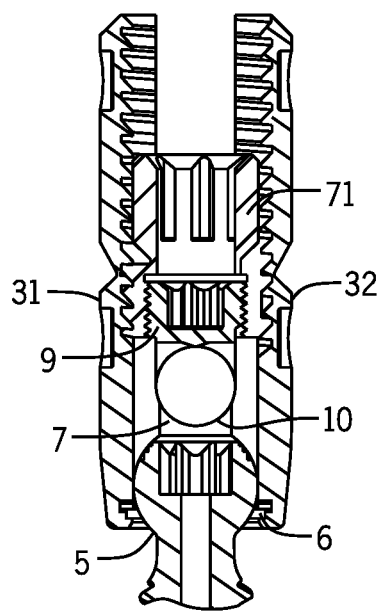
FIG. 25 is a cross section of the receiver as in FIG. 19 showing a sixth stage of the positioning of the insert in the receiver showing the closure pushing the rod downwardly into a locked position against the insert.
Figure 26:
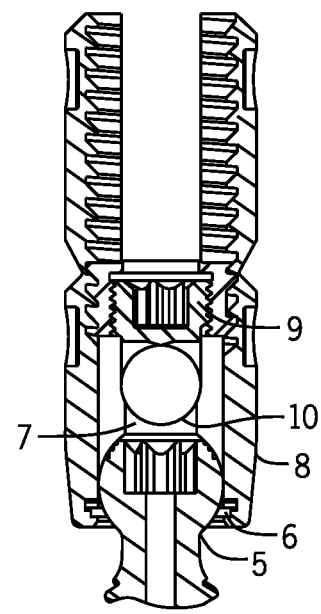
FIG. 26 is a cross section of the receiver as in FIG. 19 showing a ninth stage of the positioning of the insert in the receiver with the rod secured in place in a channel of the receiver and a head of the closure broken away.

Shown in FIG. 25, the closure is now also independently locking the rod 10. In FIG. 26, the closure 9 is fully advanced against both the insert and the rod 10 and the head 71 is broken away. The arm extensions 35 can then be broken away (not shown). At this point, the closure 9 applies pressure to the rod 10 and/or pressure insert 7 which applies pressure to the shank 5 thereby locking the shank 5 in a fixed rotational position relative to the axis A of the receiver with the shank implanted in a bone (not shown). Prior to locking the shank 5 is polyaxially rotatable relative to the receiver 8 meaning that the angle of the shank 5 may be varied with respect to the receiver 8 and the axis A.

Figure 27:
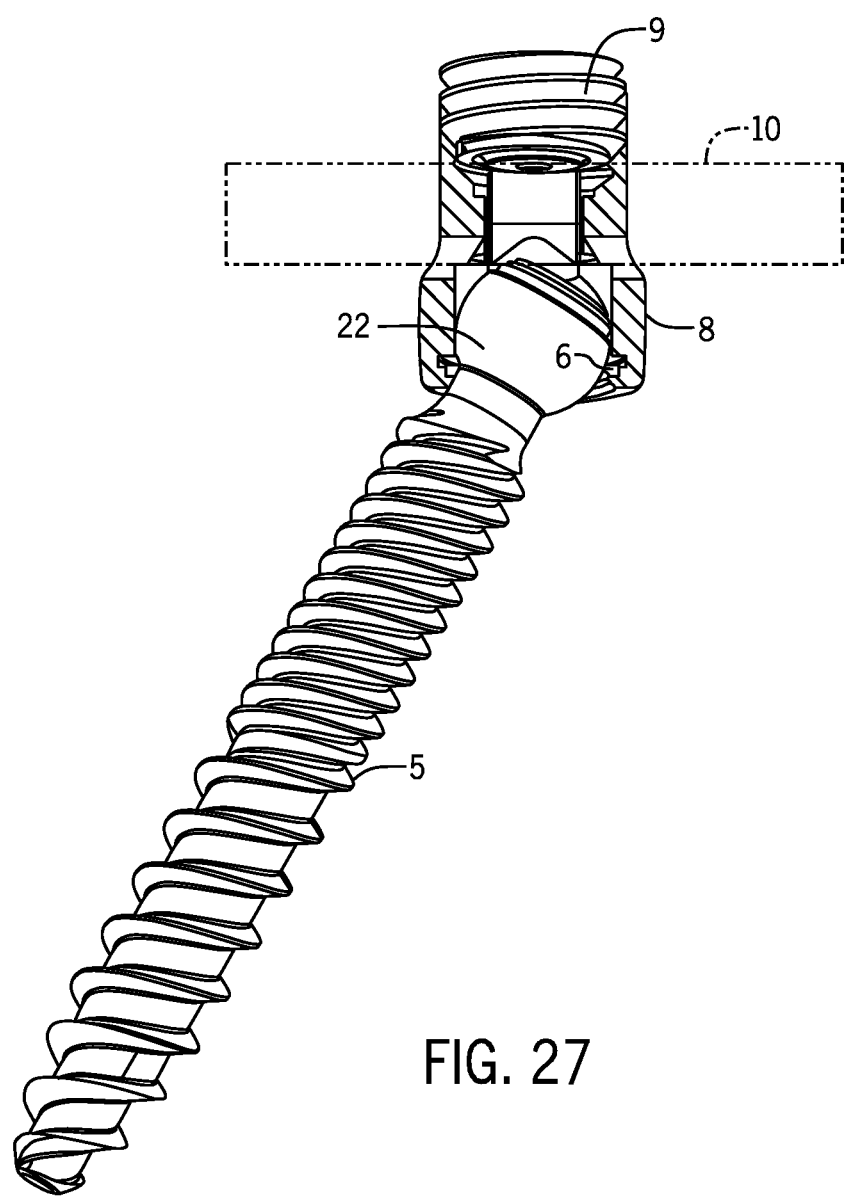
FIG. 27 is a side elevational view of the bone anchor with a rod shown in phantom and with the shank pivoted with respect to the retainer with portions removed to show detail thereof.

FIG. 27 shows an alternative locked configuration for the polyaxial positioning of the shank 5 relative to the receiver 8.

Once the insert 7 enters the receiver chamber 40, the guides 46 cooperate with the insert shoulder 65 to guide the insert 7 up and down in the receiver 8 while preventing rotation of the insert relative to the receiver 8.

Figure 28:
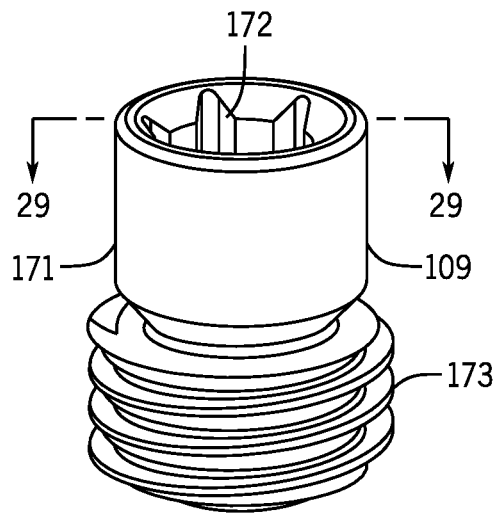
FIG. 28 is a perspective view of a second embodiment of a closure usable with the present invention.
Figure 29:
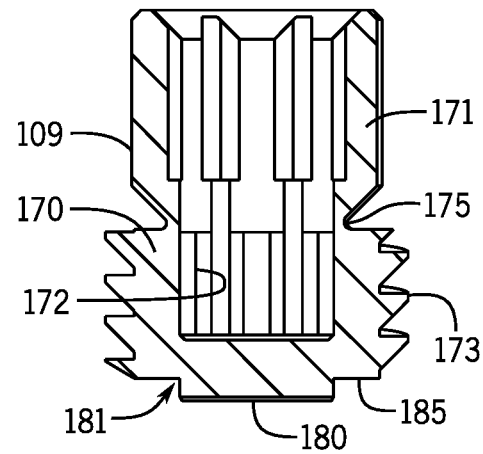
FIG. 29 is a cross sectional view of the closure of FIG. 28, taken along line 29-29 of FIG. 28.
Figure 30:
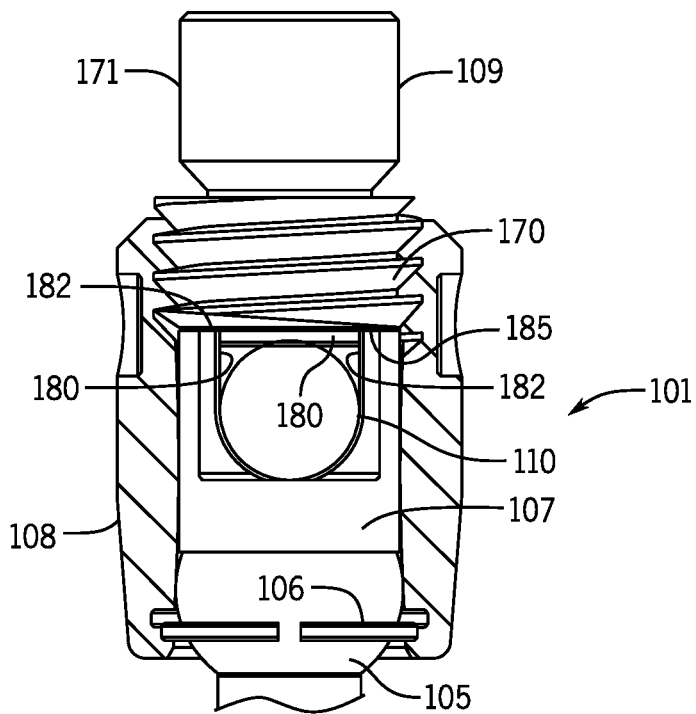
FIG. 30 is a side elevational view of a bone anchor assembly with the closure of FIG. 28 and a receiver, rod, pressure insert and retainer with the receiver partially broken away to show detail thereof.

Shown in FIGS. 28 to 30 is an alternative closure for use with the present invention generally identified by the reference numeral 109. It is shown in use in an implant assembly 101 shown in FIG. 30. The closure 109 differs in several aspects from the closure 9. In particular, the closure 9 has an outer ring with a central screw sometimes referred to as a dual innie. The present closure has a unitary body 170 and includes a break off head 171. The body 170 includes outer helical wound reverse angle threads 173 and an internal tool receiving structure 172 for driving the closure 109. The head 171 is attached to the body 170 at a break off neck 175. The head 171 is shown attached to the body 170 in FIG. 30 just prior to breaking away. Importantly, depending from the bottom of the body 170 is a solid circular ring 180 that provides a reduced radius or step down 181.

Seen in FIG. 30 is the closure 109 in a receiver 108 along with a shank 105, a shank retainer 106, a pressure insert 107 and a rod 110. The present insert 107 has two upstanding arms 180 and 181 each with a top surface 182. The arms 180 and 181 are spaced such that the ring 180 on the bottom of the closure 109 passes therebetween on assembly with a slight clearance on each side. A lower surface 185 of the closure body 170 that is radially outward of the ring 180 remains spaced from the insert arms upper surface 182 during assembly and locking. The parts of the assembly 1 and 101 and especially the receiver 8 and 108 and the insert 7 and 107 are preferably constructed of metal that is strong and resists bending or splaying of the arms of either the insert 107 or receiver 108. Preferred material of construction is any grade of titanium and most preferably, cobalt chrome.

It is to be understood that while certain forms of the present invention have been illustrated and described herein, it is not to be limited to the specific forms or arrangement of parts described and shown.

What is claimed is:

1. A pivotal bone anchor assembly for securing an elongate rod to a bone of a patient, the pivotal bone anchor assembly comprising:
    a shank having an upper capture portion and an anchor portion opposite the upper capture portion configured for fixation to the bone;
    a receiver having a top, a bottom, a longitudinal axis extending from the top to the bottom, a base defining a chamber communicating with the bottom of the receiver through a bottom opening, and a pair of upstanding arms extending upwardly from the base to define a first channel opening onto the top of the receiver and configured to receive the elongate rod, the first channel communicating with the chamber, the chamber including a circumferential expansion groove defined in part by a cylindrical sidewall and a downwardly-facing upper surface extending perpendicular to the longitudinal axis, and a circumferential locking groove below the expansion groove defined in part by a cylindrical sidewall and an upwardly-facing seating surface extending perpendicular to the longitudinal axis, the locking groove having a diameter that is less than a diameter of the expansion groove;
    an insert having an upper surface defining a second channel opening onto a top of the insert and configured to receive the elongate rod, the insert being uploadable into the chamber through the bottom opening so as to be at least partially positionable within the first channel of the receiver, the insert having an outer surface that is slidably engageable with a longitudinal alignment structure formed in the receiver to prevent rotation between the insert and the receiver and to maintain the second channel in alignment with the first channel; and
    an open retainer ring having a top surface, a bottom surface, an internal surface, and a cylindrical external surface, and having a gap extending entirely through the ring from the top surface to the bottom surface and from the internal surface to the external surface, the retainer ring being uploadable into the chamber of the receiver through the bottom opening after the insert and positionable within the circumferential locking groove of the chamber,
    wherein the upper capture portion of the shank is uploadable into the chamber of the receiver through the bottom opening after the insert and the retainer ring, in which the upward loading motion of the upper capture portion along the longitudinal axis is configured to urge the retainer ring up into the circumferential expansion groove and into expansion around the upper capture portion within the circumferential expansion groove, after which the retainer ring is configured to resiliently return to the circumferential locking groove so as to capture the upper capture portion within the chamber, and
    wherein the insert is configured to engage the upper capture portion of the shank, with the bottom surface of the retainer ring being seated against the upwardly-facing seating surface, so as to lock the angular position of the shank with respect to the receiver.

2. The pivotal bone anchor assembly of claim 1, wherein the shank is a polyaxial screw with a threaded shank.

3. The pivotal bone anchor assembly of claim 1, wherein the shank is cannulated so as to have a central opening along an entire length thereof.

4. The pivotal bone anchor assembly of claim 1, wherein the upper capture portion of the shank includes a partially spherical outer surface engageable with an underside surface of the insert.

5. The pivotal bone anchor assembly of claim 1, wherein the diameter of the cylindrical sidewall of the circumferential locking groove is substantially equal to a diameter of the cylindrical external surface of the retainer ring.

6. The pivotal bone anchor assembly of claim 1, wherein the diameter of the circumferential expansion groove is greater than a diameter of the retainer ring in a non-flexed state to allow the retainer ring to flex open within the circumferential expansion groove and allow passage of the upper capture portion therethrough during the uploading of the upper capture portion into the chamber.

7. The pivotal bone anchor assembly of claim 1, wherein the receiver further includes at least one breakoff extension extending upwardly from the upstanding arms of the receiver.

8. The pivotal bone anchor assembly of claim 1, wherein the bottom surface of the retainer ring is compressible against the upwardly-facing seating surface of the circumferential locking groove of the chamber when in the locked position.

9. The pivotal bone anchor assembly of claim 1, wherein the retainer ring is in a non-contracted state when seated against the upwardly-facing seating surface so as to lock the shank with respect to the receiver.

10. The pivotal bone anchor assembly of claim 1, wherein the insert further comprises a cylindrical base sized for uploading through the bottom opening and a pair of upstanding arms extending upwardly from the cylindrical base with opposed inner surfaces defining the second channel.

11. The pivotal bone anchor assembly of claim 10, wherein the opposed inner surfaces of the upstanding arms of the insert are configured to be substantially flush and aligned with inner surfaces of the upstanding arms of the receiver.

12. The pivotal bone anchor assembly of claim 10, wherein outer surfaces of the upstanding arms of the insert are configured for engagement with inner surfaces of the upstanding arms of the receiver upon the at least partial positioning of the insert into the first channel of the receiver so as to maintain the second channel in alignment with the first channel.

13. The pivotal bone anchor assembly of claim 12, wherein the inner surfaces of the upstanding arms of the receiver include downwardly-facing surfaces formed therein and engageable by top surfaces of the upstanding arms of the insert to restrict upward motion of the insert relative to the receiver.

14. The pivotal bone anchor assembly of claim 1, wherein the upward loading motion of the upper capture portion of the shank along the longitudinal axis is configured to urge the retainer ring into at least partial engagement with the downwardly-facing upper surface of the circumferential expansion groove.

15. The pivotal bone anchor assembly of claim 1 and further comprising the elongate rod and a closure top, wherein the closure top is configured for positioning within the first channel of the receiver above the elongate rod and in engagement with a mating structure formed into the pair of upstanding arms to apply a downward pressure to a top of the elongate rod, so as to secure the elongate rod to the bone of the patient.

16. A pivotal bone anchor assembly for securing an elongate rod to a bone of a patient via a closure top, the pivotal bone anchor assembly comprising:
   a shank having an upper capture portion and an anchor portion opposite the upper capture portion configured for fixation to the bone;
   a receiver having a top, a bottom, a longitudinal axis extending from the top to the bottom, a base defining a chamber communicating with the bottom of the receiver through a bottom opening, and a pair of upstanding arms extending upwardly from the base to define a first channel configured to receive the elongate rod, the first channel communicating with the chamber, the chamber including an upper expansion groove defined in part by a cylindrical sidewall and a downwardly-facing upper surface extending perpendicular to the longitudinal axis, and a lower locking groove below and adjacent to the upper expansion groove defined in part by a cylindrical sidewall and an upwardly-facing seating surface extending perpendicular to the longitudinal axis, the cylindrical sidewall of the lower locking groove having a diameter that is less than a diameter of the cylindrical sidewall of the upper expansion groove;
   an insert configured for uploading into the chamber through the bottom opening so as to be at least partially positionable within the first channel of the receiver, the insert having an upper surface defining a second channel configured to receive the elongate rod and an outer surface that is slidably engageable with a longitudinal alignment structure formed in the receiver to prevent rotation between the insert and the receiver and to maintain the second channel in alignment with the first channel; and
   an open retainer ring having a top surface, a bottom surface, an internal surface, and a cylindrical external surface, and having a gap extending entirely through the ring from the top surface to the bottom surface and from the internal surface to the external surface, the retainer ring being uploadable into the chamber of the receiver through the bottom opening after the insert and positionable within the lower locking groove,
   wherein the upper capture portion of the shank is uploadable into the chamber of the receiver through the bottom opening after the insert and the retainer ring, in which the upward loading motion of the upper capture portion along the longitudinal axis is configured to urge the retainer ring up into the upper expansion groove and into expansion around the upper capture portion, after which the retainer ring is configured to resiliently return to the lower locking groove, with the cylindrical external surface of the retainer ring in engagement with the cylindrical sidewall of the locking groove, so as to capture the upper capture portion of the shank within the chamber.

17. The pivotal bone anchor assembly of claim 16, wherein the insert is configured to engage the upper capture portion of the shank, with the bottom surface of the retainer ring being seated against the upwardly-facing seating surface, so as to lock the angular position of the shank with respect to the receiver.

18. The pivotal bone anchor assembly of claim 16, wherein the insert further comprises a cylindrical base sized for uploading through the bottom opening and a pair of upstanding arms extending upwardly from the cylindrical base with opposed inner surfaces defining the second channel.

19. The pivotal bone anchor assembly of claim 18, wherein outer surfaces of the upstanding arms of the insert are configured for engagement with inner surfaces of the upstanding arms of the receiver upon the at least partial positioning of the insert into the first channel of the receiver so as to maintain the second channel in alignment with the first channel.

20. The pivotal bone anchor assembly of claim 16 and further comprising the elongate rod and the closure top, wherein the closure top is configured for positioning within the first channel of the receiver above the elongate rod and in engagement with a mating structure formed into the pair of upstanding arms of the receiver to apply a downward pressure to a top of the elongate rod, so as to secure the elongate rod to the bone of the patient.

* * * * *